US00PP12609P2

(12) United States Plant Patent
Winchel

(10) Patent No.: US PP12,609 P2
(45) Date of Patent: May 7, 2002

(54) HYBRID TEA ROSE PLANT NAMED 'WINFPAGE'

(75) Inventor: Joseph F. Winchel, Harbor City, CA (US)

(73) Assignee: Coiner Nursery, Laverne, CA (US)

( * ) Notice: Subject to any disclaimer, the term of this patent is extended or adjusted under 35 U.S.C. 154(b) by 0 days.

(21) Appl. No.: 09/483,452

(22) Filed: Jan. 12, 2000

(51) Int. Cl.[7] ..... A01H 5/00
(52) U.S. Cl. ..... Plt./130
(58) Field of Search ..... Plt./130

*Primary Examiner*—Bruce R. Campell
*Assistant Examiner*—Annette H. Para
(74) *Attorney, Agent, or Firm*—Christie, Parker & Hale, LLP

(57) ABSTRACT

A hybrid tea rose plant variety producing bi-color red and light pink flowers.

1 Drawing Sheet

BACKGROUND OF THE INVENTION

The present invention relates to a new and distinct hybrid tea rose variety which was originated by my crossing as seed parent the variety known as 'Blue Nile,' believed to be patented as pollen parent an unnamed, undistributed and unpatented seedling. The varietal denomination of this new rose is 'Winfpage'.

SUMMARY OF THE INVENTION

Among the novel characteristics possessed by the new variety which distinguish it from its parents and all other varieties of which I am aware are its attractive red and pink bi-color flower coloration.

Asexual reproduction by budding of the new variety as performed in Harbor City, Calif., and Kern County, Calif., shows that the foregoing and other distinguishing characteristics come true to form and are established and transmitted through succeeding propagations. Other known forms of asexual reproduction may be also used.

COMPARISON WITH PARENT

The new variety distinguishes from its parent in flower size and color.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

The following is a detailed description of the new variety, from two year old specimens grown in Kern County, Calif., in the month of November. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

Flower:

*Habit.*—Recurrent.

*Bud.*—Size: Length about 1½ inches, width about 1¼ inches. Form: Urn shaped. Color: When sepals first divide near 46A.

*Sepals.*—About five sepals, about ½ inch wide, about 1¾ inches in length; about ½ as long as bud; serrated shape foliage, smooth texture foliage, margin irregular, about 8 appendages; color near 143C.

*Peduncle.*—Length: About ½ inch. Strength: Erect, sturdy. Color: Near 143A.

*Bracts.*—None.

Bloom:

*Size.*—About 5 inches diameter.

*Borne.*—Singly.

*Form.*—High centered, exhibition-type.

*Petalage.*—About 27 to 28.

*Color* (⅓ to ½ open).—Outer petals: Top surface near 57A; under surface near 58D. Inner Petals: Top surface near 58C; under surface near 62D. Base of petals: Near 62D.

*Color* (*fully open*).—Outer petals: Top surface near 57A; under surface near 58D. Inner petals: Top surface near 58C; undersurface near 62D. Base of petals: Near 62D. General tonality from a distance: Bi-color light red, near 57A and light pink near 62A, with white.

*Color change.*—Blooms fade slightly upon aging on the top and underside.

Petals: Imbricated, upper side satiny, underside dull; about 1 15/16 inches long and about 1¾ inches wide.

*Appearance.*—Velvety.

*Form.*—Elliptical.

*Arrangement.*—Imbricated, regularly arranged, shingle-like.

*Petaloids in center.*—None.

*Persistence.*—Petals drop off cleanly.

*Fragrance.*—Very slight fragrance.

*Lasting quality.*—About 10 days on plant; about 7 to 10 days after cutting.

Reproductive organs: About 94 anthers and 94 pistils.

*Stamens, filaments and anthers.*—Arrangement: Regularly arranged around styles. Color Stamens: Near 11C. Anthers: Near 59D.

*Pollen*.—Color: Near 17A.

*Styles*.—Uneven.

*Stigmas*.—Color: Near 11B. Hips: Globular, near 23C, seeds do not protrude.

Plant:

*Form*.—Upright, v-shaped.

*Growth*.—Average vigor, height 36 inches first season.

*Foliage*.—Compound 5 leaflets, about 3 inches long by about 1⅞ inches wide. Color: New foliage: Upper side near 59A; underside near 59A. Old foliage: Upper side near 147A; underside near 148B. Shape: Elliptic. Texture: Upper side smooth, semi-glossy; underside matte. Edge: Serrated. Serration: Serrate. Petiole: Top and bottom surface near 145C. Stipules: Slight, narrow, small. Auricle: Near 147B with near 178C coloration. Disease Resistance: Average resistance to mildew, blackspot and rust.

*Wood*.—New shoots: Near 152D, smooth. Old wood: Near 138C, smooth.

*Thorns*.—About 42 per foot. Quantity: Occasional. Form: Dorsal. Length: About 3/16 inches. Color when young: Near 11D. Position: Irregular.

*Prickles*.—Very few.

*Flower stems from last cut*.—About 4 inches.

Winter hardiness: Completely winter hardy in Kern County.

I claim:

1. A new and distinct hybrid tea rose plant of the variety substantially as shown and described.

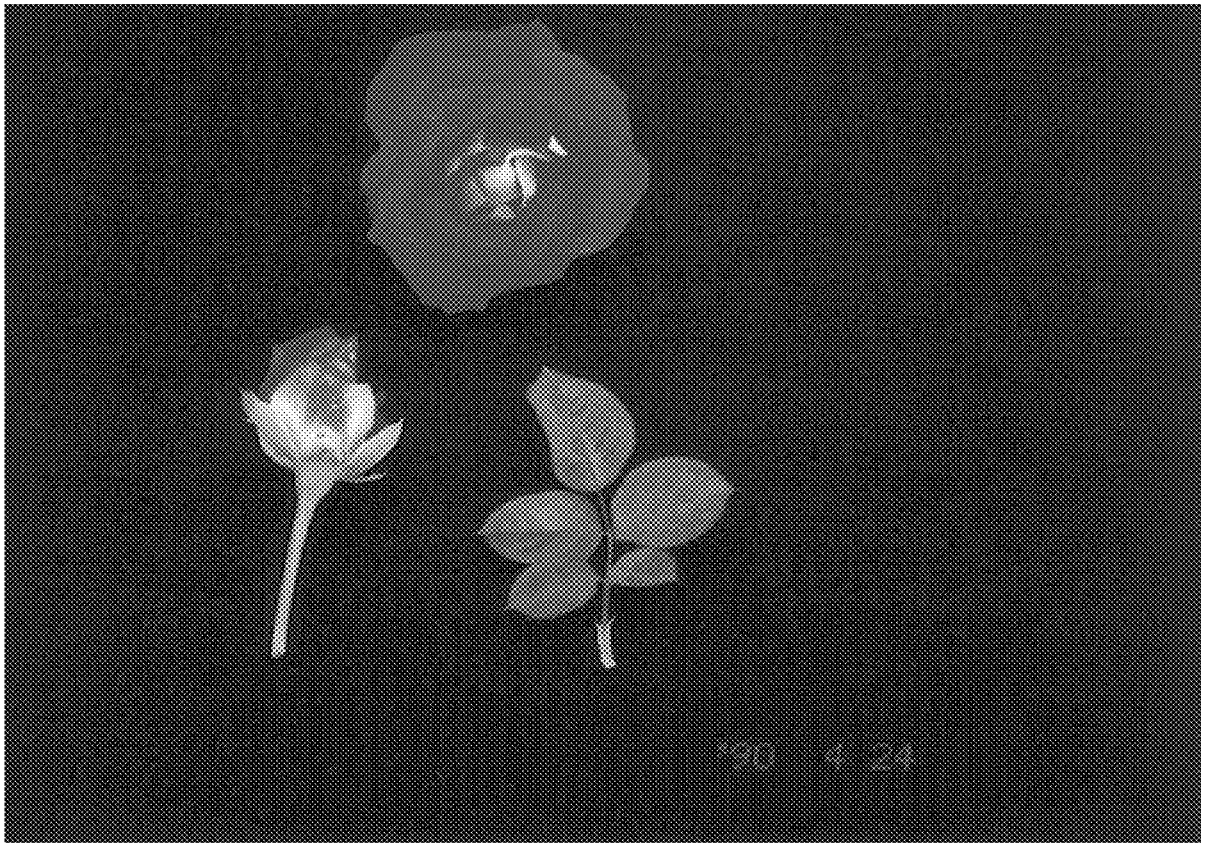

* * * * *